(12) United States Patent
Ferraresi

(10) Patent No.: US 7,758,543 B2
(45) Date of Patent: Jul. 20, 2010

(54) END-OF-USE PROTECTIVE ELEMENT FOR NEEDLES FOR PERFUSIONS, TRANSFUSIONS AND SUCH-LIKE

(76) Inventor: Federico Ferraresi, Via Matarelli 14, Giardini, 474/M, I-41100, Modena (IT)

( * ) Notice: Subject to any disclaimer, the term of this patent is extended or adjusted under 35 U.S.C. 154(b) by 788 days.

(21) Appl. No.: 10/577,335

(22) PCT Filed: Oct. 26, 2004

(86) PCT No.: PCT/EP2004/012073

§ 371 (c)(1),
(2), (4) Date: Jan. 17, 2007

(87) PCT Pub. No.: WO2005/049126

PCT Pub. Date: Jun. 2, 2005

(65) Prior Publication Data
US 2007/0213664 A1 Sep. 13, 2007

(30) Foreign Application Priority Data
Oct. 28, 2003 (IT) .................. MO2003A0292

(51) Int. Cl.
*A61M 5/00* (2006.01)
(52) U.S. Cl. .................................... 604/110
(58) Field of Classification Search .......... 604/110
See application file for complete search history.

(56) References Cited

U.S. PATENT DOCUMENTS

| 5,147,319 | A | | 9/1992 | Ishikawa et al. ............ 604/174 |
| 5,323,900 | A | | 6/1994 | Atkins et al. ................ 206/365 |
| 6,413,243 | B1 | * | 7/2002 | Geist .......................... 604/192 |
| 6,589,209 | B1 | * | 7/2003 | Dysarz ........................ 604/110 |
| 2003/0050601 | A1 | * | 3/2003 | Righi et al. ................. 604/110 |
| 2004/0111057 | A1 | * | 6/2004 | Wilkinson ................... 604/110 |

FOREIGN PATENT DOCUMENTS

| WO | WO 90/03196 | | 4/1990 |
| WO | WO 9003196 A1 | * | 4/1990 |

\* cited by examiner

*Primary Examiner*—Nicholas D Lucchesi
*Assistant Examiner*—Diva Ranade
(74) *Attorney, Agent, or Firm*—Thomas R. Vigil

(57) ABSTRACT

This invention falls into the field of devices designed to prevent medical workers after using needles on patients who may be suffering from infective pathologies transmissible via blood. A protective element is composed, at the time of production and shipping, of a first portion and a second portion reciprocally constrained by a connecting element moulded contemporaneously with the said two portions. A pan has been created inside the first portion and first ridges and second ridges have been created in the lower part of the second portion.

2 Claims, 5 Drawing Sheets

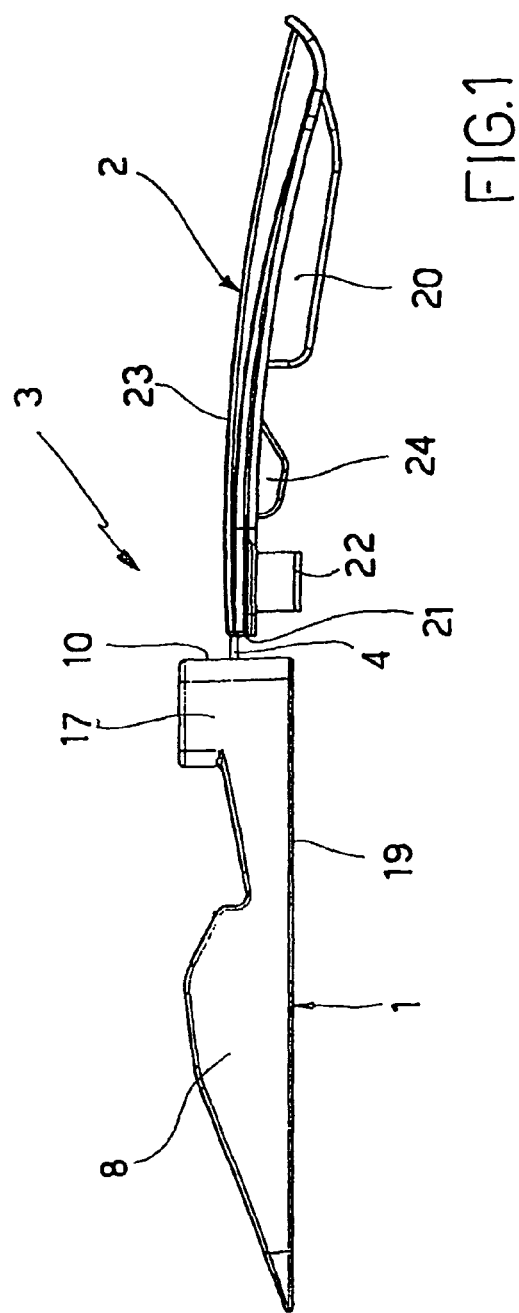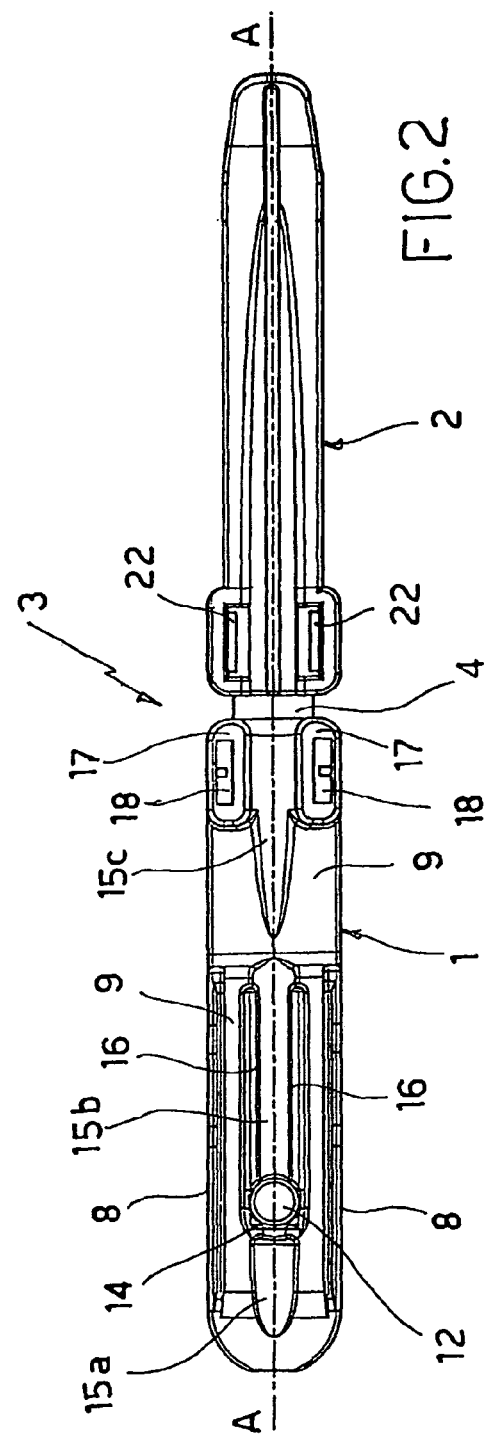

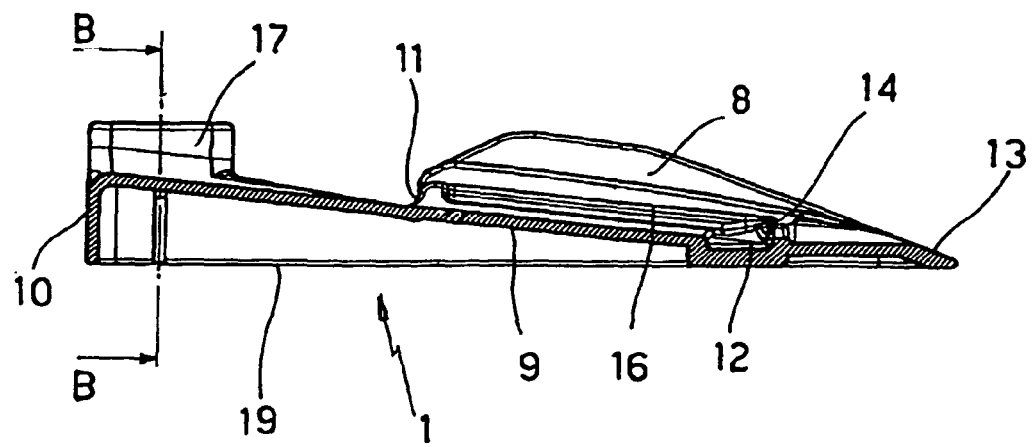
FIG.6
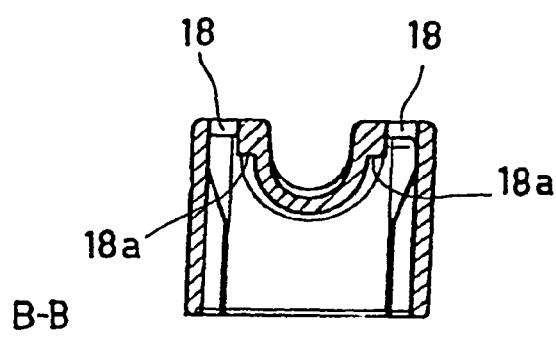
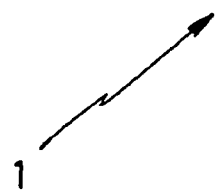
FIG.7

END-OF-USE PROTECTIVE ELEMENT FOR NEEDLES FOR PERFUSIONS, TRANSFUSIONS AND SUCH-LIKE

TECHNICAL FIELD

The invention relates to an end-of-use protective element for needles for perfusions, transfusions and suchlike.

BACKGROUND ART

Post-use protective elements have been used for some time for needles fitted with small wings, called "flaps", which are constrained integral to the said needles, designed for carrying out perfusions, phleboclysis and similar operations. The aim of these devices is to prevent the medical workers piercing themselves accidentally with the needle just used on a patient who may have a pathology transmissible via blood.

The importance this protective element holds has led to the design and production of numerous protective elements of this kind. Essentially, these are cases whose construction is designed to allow the pipe used for the adduction of the liquid to be injected into or drawn from the patient to slide inside them and to allow the needle to then be concealed inside them immediately after its use. The typology of these protective elements is essentially based on a body, which is generally a hollow cylindrical shape, having two slits, located on diametrically opposing sides, for the wings with which perfusion and transfusion needles are fitted to slide into; the said slits having, in their rear portion, a front locking element, for example a step or a small tooth; in this way the needle, after being slid back into the protective element, is trapped within the latter and cannot leave it again. Naturally, to achieve the functioning of the said locking element, this element must have a certain flexibility.

Document WO 90/03196 is known, in which various embodiments of the protective element are presented.

Although the known embodiments generally offer a good degree of safety as far as the risk of piercing after use of the needle, they have certain limits as regards to the drops of blood retained which could run down the said needle; since mere contact between mucous membranes and the infected blood constitutes a serious risk, the said limits can be considered real drawbacks.

DISCLOSURE OF INVENTION

An initial aim of this invention is to produce a protective device which, although composed of two portions which must be separate to allow them is to be fitted around the pipe to which the needle is connected, is made of a single piece at the time of production and shipping, providing for substantial transportation savings.

A further aim consists in the production of a device which, in addition to guaranteeing an effective preventative action against accidental piercing, is also able to guarantee protection against possible blood leaks from the needle after use of the said needle.

In particular, the end-of-use protective element for needles for perfusions, transfusions and suchlike in question in this invention, of the type which envisages the complete insertion and locking of a needle fitted with wings inside a protective casing, is characterised by the fact that it is composed of first portion and a second portion which are constrained together reciprocally by means of a connecting element at the time of production and shipping and which are separate at the time of use, said separation being rendered possible by the detachment of the aforesaid connecting element, and by the fact that the first portion is fitted with a pan and the second portion is fitted with at least two ridges, the said pan and the said ridges being positioned inside the respective portions in such a way that they are located on internal sides of the protective element, in reciprocally opposing positions, when the said protective element is in use; the said first portion and second portion being constrained together, when in use, via locking means and corresponding slits in the rear part of the said protective element.

This and other characteristics will better emerge in the description that follows of a preferred embodiment illustrated, purely in the form of a non-limiting example, in the drawing enclosed, in which:

FIG. 1 shows a side view of the protective element in the initial configuration;

FIG. 2 shows a top view of the element in the configuration shown in FIG. 1;

FIG. 6 shows a longitudinal view of the first portion of the protective element;

FIG. 7 shows a transversal view of the first portion in the area corresponding with the protrusions with the slit, according to the section B-B;

Figure 3:
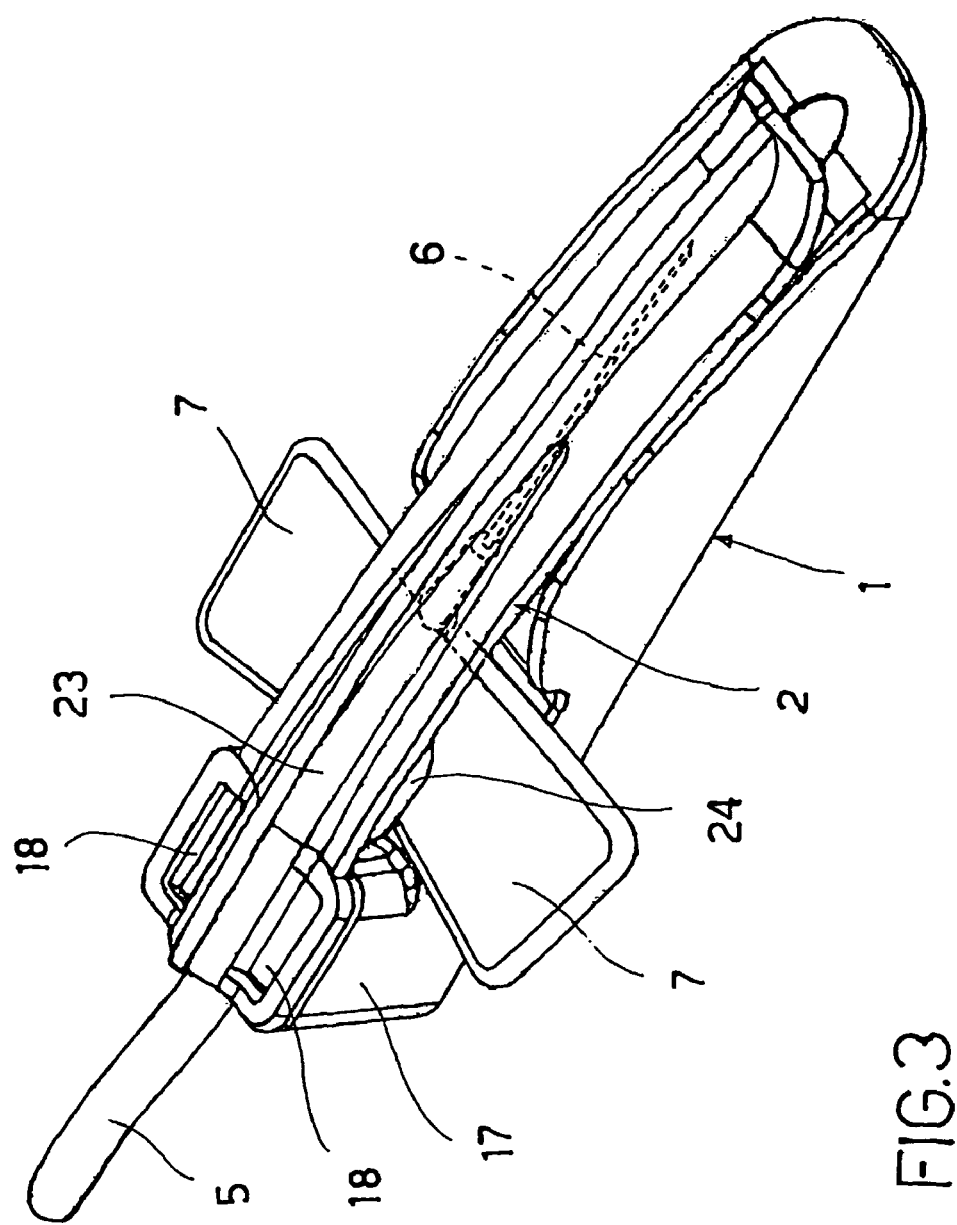
FIG. 3 shows an axonometric overview of the protective element in use, including the needle retracted inside the said element.
Figure 4:
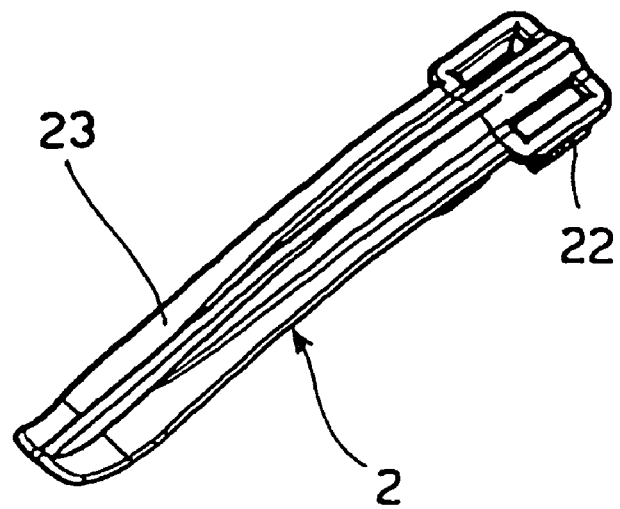
FIG. 4 shows an axonometric view of the first portion.
Figure 5:
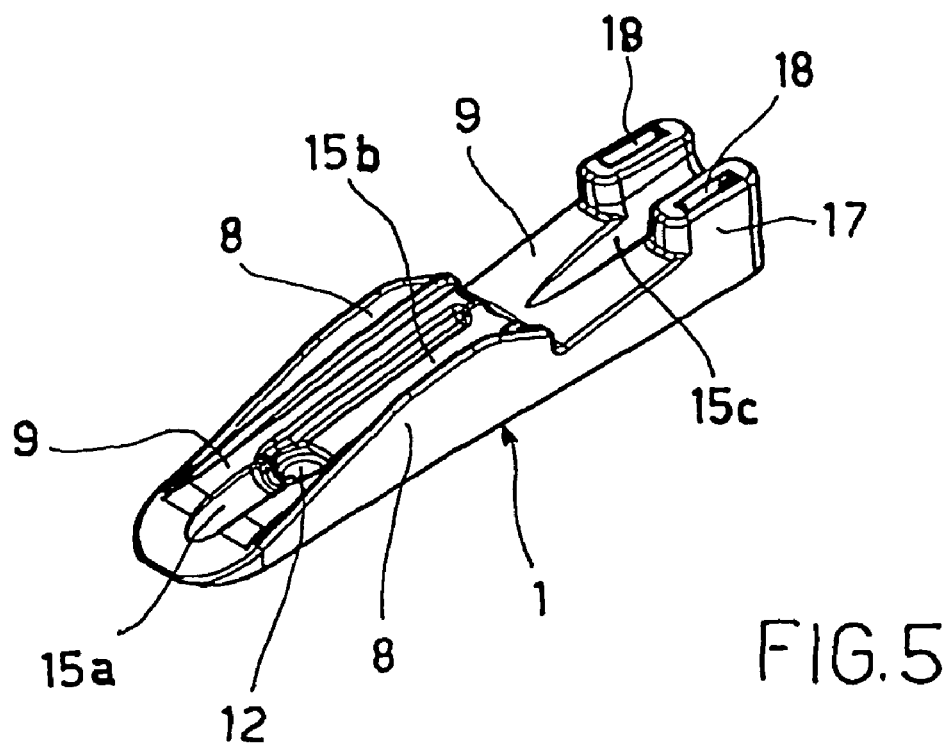
FIG. 5 shows an axonometric view of the second portion.
Figure 8:
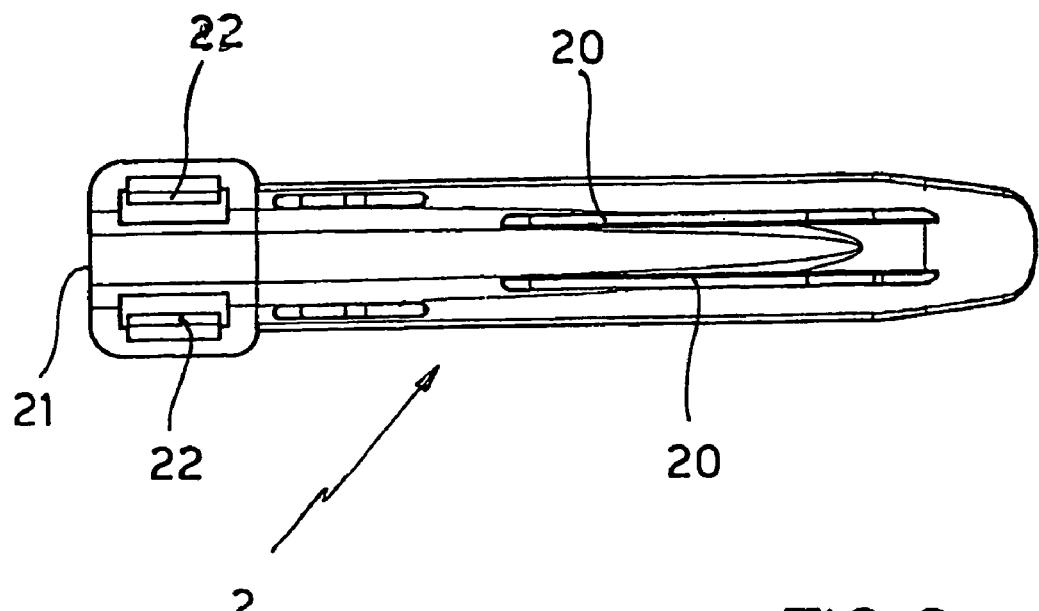
FIG. 8 shows a view in plan form of the lower part of the second portion.

With reference to the figures, 1 is a first portion and 2 is a second portion of the protective element 3; the said first and second portions are reciprocally connected by means of a connecting element 4, e.g. a tab. The protective element 3 is in the configuration shown in FIGS. 1 and 2 immediately after the moulding operation and during the transportation of the said element to the users, before it is fitted by the said users around a linking pipe 5 with a 'flap', i.e. a needle 6 fitted with wings 7. The first portion 1 has, along approximately half of its longitudinal extension, two lateral edges 8 which are raised in relation to a base surface 9, each of which is positioned on the external sides of first portion 1 with the respective external surface level with the lateral profile of the said portion. Each of the lateral edges 8 terminates, in the direction of a rear part 10 of the first portion 1, with a shoulder 11 which interrupts the vertical extension of each of the said edges. The lateral edges 8 also constitute the lateral edges of the protective device 3 in its configuration when in use, as shown in FIG. 3.

There is a pan 12 created inside the said first portion which is centred with the central longitudinal axis A-A of the first portion 1 corresponding to the longitudinal axis of the entire protective device 3 in both its extended configuration and in its configuration when in use.

The portion of the said pan facing in the direction of a front part 13 of the first portion 1 is fitted with a frontal protrusion 14. The said front part of the first portion 1 also corresponds to the front part of the protective element 3 in its configuration when in use, as shown in FIG. 3.

The first portion 1 has three grooves 15a, 15b and 15c aligned in series along the longitudinal axis A-A; in particular, the first groove 15a extends to the pan 12, the second groove 15b extends, essentially, from the said pan until it is level with the shoulders 11 and the third groove 15c extends from the area of the aforesaid shoulders to the rear part 10.

A step 16 separates, on both sides of the axis A-A, the base surface 9 from the second groove 15b.

In the area corresponding to the rear part 10 there are two protrusions 17 created, reciprocally separate, each of which is positioned on the external sides of the first portion 1 with the respective external surface level with the lateral profile of the said portion.

Each of the protrusions 17 has a slit 18 which extends vertically in relation to a resting surface 19 of the first portion 1 on the patient's skin.

18a is the lower base of each slit 18, as visible in the section in FIG. 7. Moving on to consider the second portion 2, 20 refers to the two ridges, positioned in the part of the second portion 2 designed to remain inside the protective element 3 when the said element is in use; the said ridges are reciprocally separate, parallel to the extension of the longitudinal axis A-A and equidistant from the said axis. The distance between the said two ridges corresponds to the distance between the steps 16 on the first portion 1.

Figure 9:
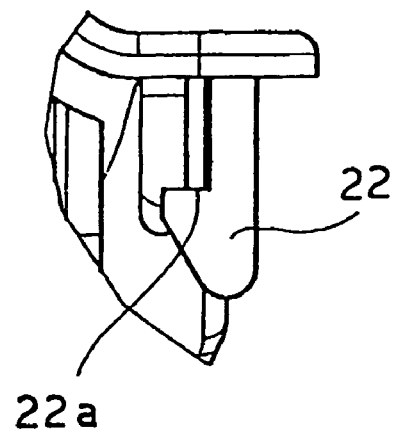
FIG. 9 shows a section detail of second portion rear part in the area corresponding with the locking means.

Laterally to a rear part 21 of the said second portion there are two locking means 22, e.g. a catch, as shown in the section in FIG. 9; the parametric size of each of the said means is just less than the size of each slit 18. 22a is the recess in each locking means 22, as visible in the section in FIG. 9.

The joining line of the connecting element 4 with the rear part 10 is positioned at a greater height than that of the resting surface 19, therefore not level with the said surface. While the joining line of the connecting element 4 with the rear part 21, instead, is essentially positioned level with the edge of an upper part 23.

24 refers to the two ridges positioned in the second portion 2 designed to remain inside the protective element 3 when this is in use; the said second ridges are reciprocally separate, parallel to the extension of the longitudinal axis A-A and equidistant from the said axis. The reciprocal distance between the said second two ridges is greater than the distance between the first two ridges 20.

The height of the second ridges 24 is such that, when the protective element 3 is in use, the distance between the said edges and the base surface 9 is slightly less than the thickness of the wing 7.

There will now follow a description of the functioning of this invention, using the references indicated in the figure.

When the protective element 3 reaches the users, it is in the configuration in which the first portion 1 and the second portion 2 are reciprocally constrained thanks to the presence of the connecting element 4; the said users will then provide for the separation of the said two portions by means of the torsion of the said connecting element, said operation being followed by the total removal of the said connecting element.

In the event that, for any reason, the users decide not to proceed with the aforesaid total removal of the connecting element 4, the latter will remain constrained to the one of the two rear parts 10 or 21.

In this case, if, following the separation of the two portions 1 and 2, the said connecting element should remain attached to the rear part 10 of the first portion 1 designed to be placed on the patient's skin, this would not interfere with the latter as the coupling line of the tab 10 is located in a raised position in relation to the resting surface 19 of the protective element 3 on the patient's skin.

In the event, though, that the tab 10 remains constrained to the second portion 2, the said tab, even if its coupling with the said second portion is essentially located at the same height as the upper surface 23, it would not interfere with the patient's skin as the said upper surface 23 is not designed to remain positioned in contact with the patient.

Once separate, the two portions 1 and 2 can be applied to the pipe 5 and constrained firmly and reciprocally by making the two catches 22 on the second portion 2 penetrate the two slits 18 of the first portion 1; with this operation, the recesses 22a snap under the respective lower bases 18a, thanks to the flexibility of the material of which the catches 22 are composed, and in such a way that the said two portions are connected together definitively and inseparably. Naturally, the clearance between the reciprocally constrained portions 1 and 2 enables the pipe 5 to compulsorily slide through the space delimited by the grooves 15a, 15b, 15c and the first ridge 20.

The functioning of the protective element 3 will not be talked about at length with regards to the insertion of a needle 6 into the said element once used and after its extraction from the patient's skin, as these are commonly known techniques; it should only be noted that the flap, i.e. the set comprising the needle 6 and the wings 7, when completely inserted into the said protective element, remains locked in the said element thanks to the interaction between the front edge of the said wings and the shoulders 11.

When the needle 6 is completely inserted in the protective element 3, the position of the needle point coincides with the position of the pan 12 and therefore any drops of blood that may flow out of the said needle would settle in the said pan without flowing out of the protective element 3.

It should also be noted that the function performed by the frontal protrusion 14, which, in addition to constituting a shoulder for the point of the needle 6, also constitutes a further barrier against blood leaking from the protective element 3.

Still with the aim of preventing blood leaking from the protective element 3, the said leaks are also averted laterally: in fact, when the two portions 1 and 2 are constrained reciprocally around the pipe 5, the lower edges of the two first ridges 20 present in the lower part of the second portion 2 are pressed against the respective steps 16 located on the first portion 1.

In addition to this, the lower edges of the second ridges 24, again when the two portions 1 and 2 are reciprocally constrained around the pipe 5, by flattening the wings 7 against the base surface 9, prevent blood leaking out laterally from the protective element 3 in the area corresponding with the groove 15c thanks to the forced adherence of the lower surface of the said wings against the said base surface.

In conclusion, when the needle 6 is completely retracted into the protective element 3, any drops of blood from the said needle do not translate into leaks from the said protective element either in the area corresponding with its front part 13 or in the area corresponding with the lateral edges 8. When the needle 6 is completely retracted into the protective element 3 it cannot be extracted intentionally, not even laterally, thanks to the presence of the first ridges 20, which delimit the lateral profile of the needle 6, and to the second ridges 24, which flatten the wings 7 against the base surface 9.

A first advantage offered by the protective element in question in this invention consists in the fact that the said element, although composed of two portions which must be separate to allow it to be fitted around the pipe to which the needle is connected, it constitutes a single piece at the time of production and shipping, so providing for substantial transportation savings.

A second advantage consists in the fact that blood leaks are prevented from the front part of the protective element 3 thanks to the existence of the internal pan 12.

A further advantage consists in the fact that the residual blood is prevented from leaking from the lateral parts of the protective element 3 thanks to the existence, on the second portion of the said protective element, of both the first ridges 20, which press against the corresponding steps 16 positioned in the opposing first portion 1, and the second ridges 24, which push the wings of the flap against the base surface 9.

A still further advantage consists in the fact that it is impossible to extract the needle from the protective element laterally when said needle is in the use configuration, thanks again to the presence of the said first ridges 20.

I claim:

1. An end-of-use protective element (3) for needles for perfusions, transfusions and suchlike which envisages the complete insertion and locking of a needle (6) fitted with wings (7) within a protective case, characterised by the fact that the said element is composed of a first portion (1) and a second portion (2) which are reciprocally constrained by means of a connecting element (4) at the time of production and shipping and which are separate at the time of use, said separation being rendered possible by the detachment of the said connecting element, and by the fact that the first portion (1) is fitted with a pan (12) and the second portion is fitted with at least two first ridges (20) and at least two second ridges (24), said pan and said first and second ridges being positioned in the respective portions in such a way that they are located on the internal sides of the protective element (3), in a reciprocally opposing position, when the said protective element is in use; the first and second portions being constrained together, when in use, via locking means (22) and corresponding slits (18) in the rear part of the said protective element, the pan (12) being centered with the longitudinal central axis of the first portion (1), said axis corresponding to the longitudinal central axis of the first portion (1), said axis corresponding to the longitudinal axis of the entire protective device (3) in both its extended configuration and its use configuration; said pan being designed to act as a container for the drops of residual from said needle (6) after its use and its retraction into said protective element, a frontal protrusion (14) being positioned in front of said pan (12) facing the front part (13); said protrusion being designed to constitute bath a shoulder for the point of the needle (6) and a further barrier against blood leaking from the protective element (3), in the area corresponding with its front part, the height of the first ridges (20) being equal to the distance, when the protective element (3) is in use, between the lower surface of the second portion (2) and the steps (16) on the first portion (1); said height being designed to permit, when the protective element (3) is in use, the co-operation to prevent blood leaking from the protective element (3) in the area corresponding with the external edges (8) of said protective element, the distance between the second ridges (24) corresponding with the distance between the steps (16) and a groove is created (15a, 15b, 15c) on a base surface (9) which extends, essentially, along the entire length of the first portion (1) and is designed to remain inside the said protective element when the latter is in use, the height of the second ridges (24) being equal to the distance that exists, when then the protective element (3) is in use, between the lower surface of the second portion (2) and the base surface (9) of the said protective element minus the thickness of the wings (7); said height being designed to permit, when the protective element (3) is in use, cooperation between the said second ridges with the upper surface of the said wings; said cooperation being designed to constitute a further protective element against the possibility of blood leaking out from the protective element (3) laterally in the area corresponding with the groove (15c), each step (16) separating the base surface (9) from the groove (15b) on both sides of the central longitudinal axis of the first portion (1).

2. A protective element according to claim 1, characterised by the fact that that first portion (1), the second portion (2) and the connecting element (4) are created by a moulding process in a single operation.

* * * * *